(12) United States Patent
Gesler, III

(10) Patent No.: US 8,550,418 B2
(45) Date of Patent: Oct. 8, 2013

(54) SYRINGE HANGER

(75) Inventor: William G. Gesler, III, New Husdson, MI (US)

(73) Assignee: Curlin Medical, Inc., East Aurora, NY (US)

( * ) Notice: Subject to any disclaimer, the term of this patent is extended or adjusted under 35 U.S.C. 154(b) by 116 days.

(21) Appl. No.: 13/127,519

(22) PCT Filed: Nov. 9, 2009

(86) PCT No.: PCT/US2009/063689
§ 371 (c)(1),
(2), (4) Date: Aug. 11, 2011

(87) PCT Pub. No.: WO2010/054290
PCT Pub. Date: May 14, 2010

(65) Prior Publication Data
US 2011/0290973 A1    Dec. 1, 2011

Related U.S. Application Data

(60) Provisional application No. 61/198,905, filed on Nov. 10, 2008.

(51) Int. Cl.
*F16B 45/00*    (2006.01)
(52) U.S. Cl.
USPC ........ 248/308; 248/691; 211/113; 211/85.13; 211/70.6

(58) Field of Classification Search
USPC ......... 248/690, 691, 692, 301, 303, 304, 305, 248/306, 308, 339; 224/269, 251, 224/148.4–148.6; 211/113, 85.13, 70.6
See application file for complete search history.

(56) References Cited

U.S. PATENT DOCUMENTS

| | | | |
|---|---|---|---|
| 2,253,444 A | 8/1941 | Muller | |
| 2,472,116 A | 6/1949 | Maynes | |
| 2,491,978 A | 12/1949 | Helfman et al. | |
| 2,500,881 A * | 3/1950 | Stader | 211/85.3 |
| 3,692,269 A * | 9/1972 | Hales | 248/691 |
| 4,073,457 A | 2/1978 | Batts et al. | 248/340 |
| 4,911,392 A * | 3/1990 | Fast | 248/220.31 |
| 4,932,571 A * | 6/1990 | Blanchard | 223/89 |
| 4,943,026 A * | 7/1990 | Fildan | 248/339 |
| 5,005,790 A * | 4/1991 | Harris, III | 248/75 |
| 5,032,117 A | 7/1991 | Motta | |
| 6,059,241 A * | 5/2000 | Martone | 248/230.1 |
| 6,062,521 A * | 5/2000 | Kelley et al. | 248/339 |
| 6,565,054 B2 | 5/2003 | Weesner et al. | |
| 7,296,772 B2 * | 11/2007 | Wang | 248/309.1 |

* cited by examiner

*Primary Examiner* — Alfred J Wujciak
(74) *Attorney, Agent, or Firm* — Hodgson Russ LLP

(57) ABSTRACT

A syringe holder is provided for mounting syringe while the syringe is distributing fluid. The syringe holder includes a hook, a main body, and a receiver. The receiver is operatively configured to deploy away from the main body when the syringe is disposed in the receiver.

9 Claims, 2 Drawing Sheets

SYRINGE HANGER

CROSS REFERENCE TO RELATED APPLICATION

This application claims the benefit of U.S. Provisional Patent Application Ser. No. 61/198,905 for a SYRINGE HANGER, filed on Nov. 10, 2008, which is hereby incorporated by reference in its entirety. This claim is made under 35 U.S.C. §119(e); 37 C.F.R. §1.78; and 65 Fed. Reg. 50093.

TECHNICAL FIELD OF INVENTION

The present disclosure relates generally to a device for mounting a syringe.

BACKGROUND OF INVENTION

As is traditionally known in the art, syringes are used to administer fluid to a body. At times, syringes may remain connected to a patient as fluid is slowly administered to the patient's body. Common solutions to maintain the connection include attaching the syringe to a bedside post using tape or placing the syringe on already existing medical equipment. However, such methods may result in the syringe not being adequately secured, or the syringe not being oriented in an appropriate manner for the fluid to be slowly administered to the patient through a line or tube to the patient.

The drainage bags used in administering fluids to patients may be held by a hanger. Such hangers may also include a structure to which the syringe is affixed to. However, the hooks and holders that are traditionally used in such hangers provide little restraint against movement of a small structure, such as the syringe. Such movement may also deleteriously affect the movement of the fluid from the syringe to the patient. Moreover, the pre-existing hooks and hangers that are primarily used for supporting bags are generally inconvenient to use given that a syringe is much smaller in construction than the drainage bags.

SUMMARY

Disclosed herein is a syringe holder for mounting syringe while the syringe is distributing fluid. The syringe holder includes a hook, a main body, and a receiver. The receiver is operatively configured to deploy away from the main body when the syringe is disposed in the receiver.

BRIEF DESCRIPTION OF THE DRAWINGS

Features and advantages of embodiment(s) of the present disclosure will become apparent by reference to the following detailed description and drawings, in which like reference numerals correspond to similar, though perhaps not identical components. Reference numerals having a previously described function may or may not be described in connection with other drawings in which they appear.

DETAILED DESCRIPTION

Embodiments of a syringe holder are disclosed herein. The syringe holder in the present disclosure may be a single piece design that can be manufactured relatively easily and cost effectively. The syringe holder may also be packaged together with the administration set, thereby providing added convenience to a user. Still further, syringe holder may be disposable. In the embodiments disclosed herein, the disposable syringe holder securely mounts a syringe as it is dispensing fluid to a patient.

Figure 1:
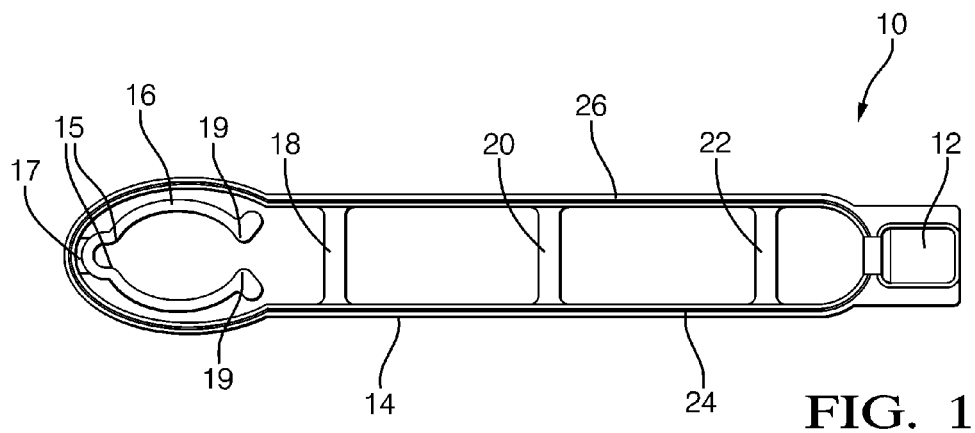
FIG. 1 is an illustration of a plan view of an embodiment of the syringe holder prior to being deployed for use.

As shown in FIG. 1, an embodiment of the syringe holder 10 is depicted. This embodiment of the syringe holder 10 includes a hook 12, a main body portion 14, and a receiver 16. The embodiment of the syringe holder 10 illustrated in FIG. 1 is a single piece syringe holder that is molded out of a polymer material. Non-limiting examples of such materials include olefin materials that are compatible with various forms of medical sterilization. Olefin materials may be particularly suitable for use with EtO, gamma or electron-beam (e-beam) sterilization techniques. It is to be understood that the material selected is flexible enough to enable the syringe holder to bend just enough to press the syringe plunger against a lattice of the device, resulting in a vertically hanging syringe, and resilient enough to enable the syringe holder to return to its original stowed position.

Figure 2:
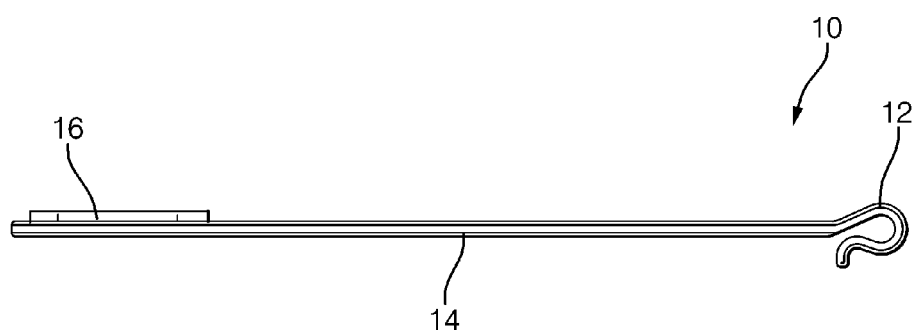
FIG. 2 is an illustration which shows a side view of an embodiment of the syringe holder prior to deployed for use.

Referring now to FIG. 2, a side view of an embodiment of the syringe holder 10 is shown where the syringe holder 10 is a one piece plastic design such that the hook 12, the main body 14 and the receiver 16 are integral to one another. FIG. 2 shows the syringe holder 10 in the stowed position such that the receiver 16 is not yet deployed away from the main body 14. The illustrated embodiment is a non-limiting example and it is to be understood that the hook 12, the main body portion 14 and the receiver 16 may be separate components and are not necessarily integral components as shown.

Figure 3:
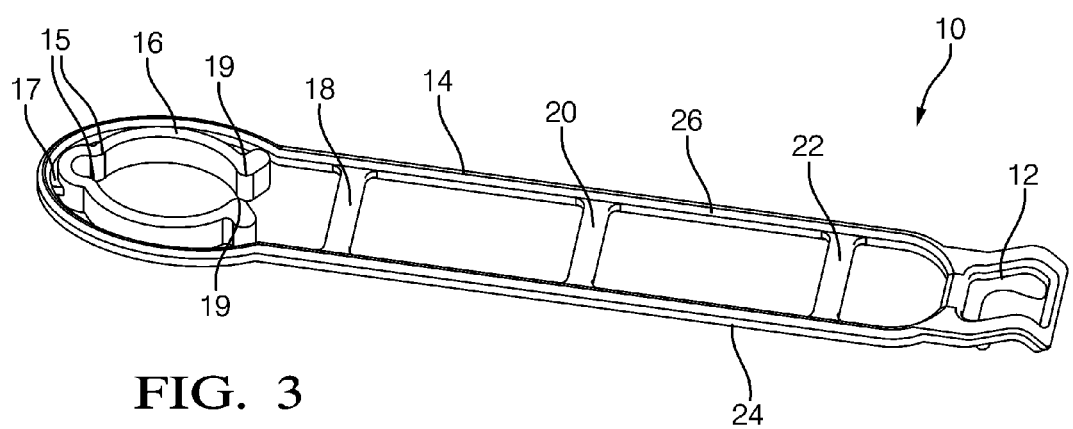
FIG. 3 is an illustration which shows an isometric view of an embodiment of the syringe holder prior to being deployed for use.
Figure 4:
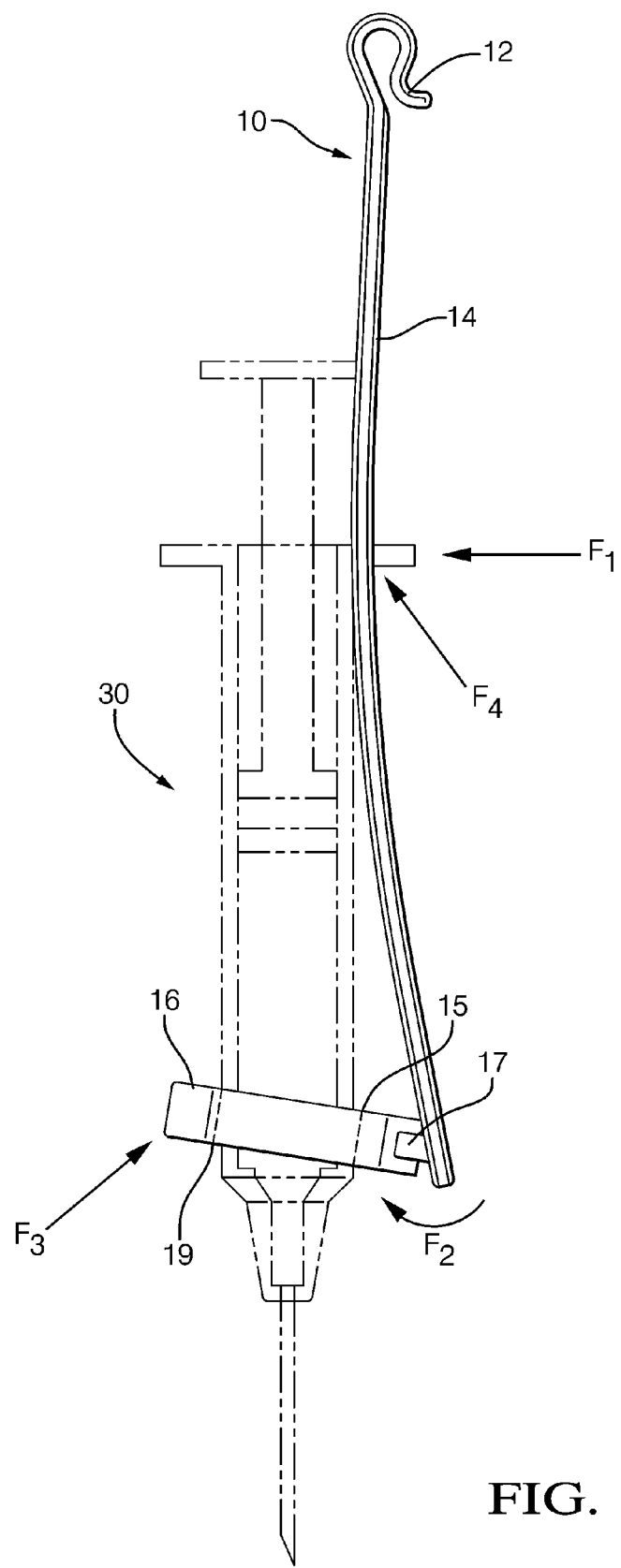
FIG. 4 is an illustration which shows a side view of an embodiment of the syringe holder deployed for use.

The hook 12 as shown as a non-limiting example in FIGS. 1-4 may be at an angle relative to main body portion 14 to allow for proper alignment of the syringe 30 when the syringe is implemented as shown in FIG. 4. It is to be understood that hook 12 is intended to engage with a mounting post or other horizontal member so that the syringe hanger 10 will be mounted vertically, where hook 12 is at the top when the syringe hanger 10 is in use. The hook 12, when in use, is intended to attach to a mounting member (not shown) such as bag holder. In one embodiment, the hook 12 snaps onto a standard IV bag pole loop. The hook 12 is an open hook 12 which provides the user with the ability to hang the syringe holder 10 in any open area on a mounting structure. As an alternative, the hook 12 may be a closed hook (not shown). However, it is to be understood that a closed hook (not shown) may require a user to thread the syringe hanger 10 onto a mounting surface, and thus may present some difficulty if other components are mounted on the same structure. As such, in some instances use of a closed hook may require removal of other components in order to thread the closed hook onto a structure.

The main body portion 14 may be integral to the hook 12, and when syringe holder 10 is in use, the main body portion 14 is disposed below the hook 12. The main body portion 14, as seen in FIGS. 1 and 3, may have cross members 18, 20, 22 that connect the sides 24, 26 (also referred to herein as lateral members) of main body portion 14. It is also to be understood that the configuration of main body portion 14 shown in the Figures is a non-limiting example of the main body portion 14, and that the main body portion 14 may be a solid strip of material that hangs in a vertical direction just below hook 12. When in use, the cross members 18, 20, 22 are oriented in a horizontal direction and are operatively configured to provide stability to lateral members 24, 26. The lateral members 24, 26 of the main body portion 14 are oriented in a vertical direction with respect to the direction of gravity when the syringe holder 10 is in use. Cross members 18, 20, 22 may also serve to secure the top of a syringe (not shown) in the vertical direction by providing an abutment to the top of a syringe. It is to be understood that a single cross member may be used to provide vertical support to the syringe itself, and to provide stability between the lateral sides of the syringe holder. In the alternative, multiple cross members 18, 20, 22 may be used to provide such vertical support to the syringe, and to provide horizontal stability between the lateral sides of the syringe holder. The cross members 18, 20, 22 prevent excessive splaying of the lateral sides 24, 26 of the syringe holder.

With reference to FIGS. 1-3 together, the receiver 16 may be integral to the syringe holder 10. As indicated, when the syringe holder 10 is in use, it is oriented in a vertical direction where the hook 12 is mounted to a structure, the main body 14 is disposed below the hook 12, and the receiver 16 is disposed below main body 14. It is further to be understood that receiver 16 is intended to deploy outward away from the main body 14 to hold the base portion of the syringe 30, which is best shown in FIG. 4. Accordingly, the receiver 16 provides vertical support to the base portion of the syringe, and the lateral sides 24, 26 of the main body 14 secure the syringe in the lateral direction. Therefore, the syringe, as it is mounted in syringe holder 10, is held in a substantially vertical direction as the syringe is administering fluid to a patient.

The receiver 16 shown in FIGS. 1 and 4 includes two opposing C-shaped members adapted to cradle the base of the syringe to support the syringe in a substantially upright position. However, it is to be understood that the receiver 16 may be a variety of configurations, such as a circular design or a horizontal platform which provides vertical support to the base portion of the syringe when it is hanging in a vertical direction. It is to be understood that the receiver 16 may be configured to loosely but securely clamp a 10 cc syringe or firmly clamp a 60 cc syringe. In some instances, the receiver 16 is configured with the negative shape of the syringe such that it may be folded out to accept the syringe. The receiver 16 may also be configured so that it does not visually obstruct the fluid containing portion of the syringe (not shown) when the syringe 30 is engaged in the hanger/holder.

The receiver 16 includes a hinged portion 17 that connects the receiver 16 to the main body 14. The hinged portion 17 may be integrally molded with the main body 14 and adapted to allow the receiver 16 to be rotatably deployed downward away from the main body 14. The hinge portion 17 is also adapted to urge the receiver 16 rotatably back into its pre-deployment or stowed position as shown in FIG. 1. The receiver also includes a first abutment portion 15 which is adapted to engage a rear portion of syringe 30. The receiver also includes a second abutment portion 19 axially spaced apart from the first abutment portion 15, in which the second abutment portion 19 is adapted to engage a front portion of the syringe 30.

Best shown in FIG. 4 is a syringe 30 disposed within the syringe holder 10, in which the receiver 16 is rotatably deployed downward away from the main body 14. The rear portion of the syringe engages the first abutment portion 15 of the receiver 16, thereby pushing the lower portion of the main body 14 apart from the syringe and flexing the upper portion of the main body 14 toward the rear portion of the syringe 30. The flexed upper portion of the main body 14 applies a lateral force (F1) onto the back of the syringe. The hinge 17 induces a rotational moment causing the first and second abutment portions 15, 19 to apply an angular upward force (F2, F3) against the rear and front portions of the syringe, respectively. A typical syringe includes a flange which can be support by one of the multiple cross members 18, 20, 22, which applies a vertical force (F4). The combination of the engagements of the upper portion of the main body 14, the first abutment portion 15, the second abutment portion 19, and at least one of the lateral supports 18, 20, 22 against the syringe 30 allows the syringe 30 to be securely held in a substantially vertical position.

The integral, one piece plastic design is a non-limiting example of the hanger/holder 10, and it is to be understood that separate components may make up the syringe holder 10 where such components are fastened together. It is to be understood that a one piece plastic design may simplify manufacturing and packaging with a disposable syringe and providing ease of implementation for a user. The syringe hanger 10 disclosed herein may also be configured to fit any standard IV set pouch, or may be made smaller that is desirable.

While several embodiments have been described in detail, it will be apparent to those skilled in the art that the disclosed embodiments may be modified. Therefore, the foregoing description is to be considered exemplary rather than limiting.

What is claimed is:

1. A syringe holder comprising:
   a main body having a first end and a second end;
   a hook disposed onto said first end; and
   a receiver disposed onto said second end, the receiver being in a first position in a rest state, and configured to rotate outward from said main body to a second position when deployed to receive a portion of a syringe in a deployed state;
   wherein the receiver includes a first abutment portion, a second abutment portion axially spaced from said first abutment portion, and a hinge adapted to rotationally urge said receiver upward and inward toward said main body in the deployed state, creating a biasing force for holding the syringe; wherein the second position, the biasing force urges the syringe against the main body, and wherein in the second position, the main body is flexed.

2. The syringe holder as defined in claim 1 wherein the hook, the main body and the receiver constitute a single piece unit.

3. The syringe holder as defined in claim 2 wherein the syringe holder is molded from a polymer material.

4. The syringe holder as defined in claim 3 wherein the main body further comprises at least one cross member, a first lateral member and a second lateral member.

5. The syringe holder as defined in claim 4, wherein said main body defines a substantially elongated shape disposed along an axis, and where said first abutment portion is axially aligned with said second abutment portion along said axis when said receiver is in said pre-deployment position.

6. The syringe holder as defined in claim 1 wherein in the first position, the main body lies substantially along a single plane.

7. The syringe holder as defined in claim 6 wherein in the second position, at least a portion of the main body is bent away from the single plane.

8. The syringe holder as defined in claim 6 wherein in the second position, at least a portion of the main body curves away from the single plane.

9. The syringe holder as defined in claim 6 wherein the receiver lies substantially along a single plane, the single plane of the receiver being substantially parallel to the single plane of the main body.

* * * * *

UNITED STATES PATENT AND TRADEMARK OFFICE
CERTIFICATE OF CORRECTION

PATENT NO.       : 8,550,418 B2          Page 1 of 1
APPLICATION NO. : 13/127519
DATED            : October 8, 2013
INVENTOR(S)      : William G. Gesler, III It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 209 days.

Signed and Sealed this

Fifteenth Day of September, 2015

Michelle K. Lee
*Director of the United States Patent and Trademark Office*